(12) United States Patent
Kazimierczuk et al.

(10) Patent No.: US 7,528,259 B2
(45) Date of Patent: May 5, 2009

(54) DERIVATIVES OF 4,5,6,7-TETRABROMOBENZIMIDAZOLE AND METHOD OF THEIR PREPARATION

(75) Inventors: Zygmunt Kazimierczuk, Warszawa (PL); Lorenzo A. Pinna, Padua (IT); Flavio Meggio, Padua (IT); Mariola Andrzejewska, Warszawa (PL)

(73) Assignee: Selvita SP. Z O. O., Kraków (PL)

( * ) Notice: Subject to any disclaimer, the term of this patent is extended or adjusted under 35 U.S.C. 154(b) by 73 days.

(21) Appl. No.: 10/599,499

(22) PCT Filed: Mar. 29, 2005

(86) PCT No.: PCT/PL2005/000022

§ 371 (c)(1),
(2), (4) Date: Sep. 29, 2006

(87) PCT Pub. No.: WO2005/092866

PCT Pub. Date: Oct. 6, 2005

(65) Prior Publication Data

US 2007/0213385 A1 Sep. 13, 2007

(30) Foreign Application Priority Data

Mar. 29, 2004 (PL) ..................... 366690

(51) Int. Cl.
*A61K 31/4184* (2006.01)
*C07D 235/30* (2006.01)
(52) U.S. Cl. ................... 548/307.4; 514/388
(58) Field of Classification Search ............... 548/307.4
See application file for complete search history.

(56) References Cited

U.S. PATENT DOCUMENTS 3,705,174 A 12/1972 Fisher et al.

FOREIGN PATENT DOCUMENTS

WO 03/030902 A1 4/2003

OTHER PUBLICATIONS

Pagano et al., Journal of Medicinal Chemistry (2004), 47(25), pp. 6239-6247.*
Pagano et al., Biochemical and Biophysical Research Communications (2004), 321(4), pp. 1040-1044.*
Golub et al., Science, vol. 286, Oct. 15, 1999, pp. 531-537.*
Pagano Mario A, et al., Optimization of Protein Kinase CK2 Inhibitors Derived from 4,5,6,7-Tetrabromobenzimidazole, J. Med. Chem., Nov. 2, 2004, pp. 6239-6247, 2004-47, American Chemical Society, Washington D.C., USA.
Pagano Mario A et al, 2-Dimethylamino-4,5,6,7-tetrabromo-1H-benzimidazole: a novel powerful and selective inhibitor of protein kinase CK2, Biochem. Biophys. Res. Commun., Sep. 3, 2004, pp. 1040-1044, Elsevier, New York, USA.
Andrzejewska Mariola et al., Polyhalogenobenzimidazoles: Synthesis and Their Inhibitory Activity against Casein Kinases, Bioorg. Med. Chem., Sep. 1, 2003, pp. 3997-4002, Pergamon, New York, USA.

* cited by examiner

*Primary Examiner*—Laura L. Stockton
(74) *Attorney, Agent, or Firm*—Matthias Scholl, PC; Matthias Scholl

(57) ABSTRACT

Taught herein are new derivatives of 4,5,6,7-tetrabromobenzimidazole of Formula 1

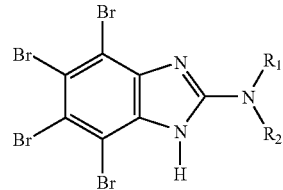

Formula 1 wherein $R_1$ is a hydrogen or an aliphatic group, and $R_2$ is an aliphatic group, optionally substituted with a hydrogen or a substituent such as a hydroxyl group or substituted amino group, and a method of their preparation.

20 Claims, 1 Drawing Sheet

DERIVATIVES OF 4,5,6,7-TETRABROMOBENZIMIDAZOLE AND METHOD OF THEIR PREPARATION

CROSS-REFERENCE TO RELATED APPLICATIONS

This is a National Stage Application of International Patent Application No. PCT/PL 2005/000022, with an international filing date of Mar. 29, 2005, which is based on Polish Patent Application No. P.366690, filed Mar. 29, 2004. The contents of both of these specifications are incorporated herein by reference.

BACKGROUND OF THE INVENTION

1. Field of the Invention

This invention relates to new derivatives of 4,5,6,7-tetrabromobenzimidazole and a method of their preparation.

2. Description of Related Art

An unsubstituted 2-amino-4,5,6,7-tetrabromobenzimidazole found in fruits as a product of degradation of the anthelmintic agent Benomyl (Pease and Gardiner, 1969), is known in the art. Its structure has been proposed on the basis of a mass spectral analysis. However, its synthesis has not yet been reported.

From US Patent Application Publication No. 2003/0027842A1 known are 2-hydroxy-4,5,6,7-tetrabromo-benzimidazole, obtained by bromination of 3-carboxy-4,6,7-tribromo-2-hydroxybenzimidazole, and 1-alkyl-4,5,6,7-tetrabromobenzimidazole, prepared by alkylation of 4,5,6,7-tetrabromobenzimidazole with alkyl halide in alkaline solution.

Halogeno derivatives of benzimidazole exhibit many interesting biological properties. It is known that derivatives of 2-trifluorobenzimidazole as well as some derivatives of bromobenzimidazoles have marked antiprotozoic, antibacterial and antiviral activity (Navarete-Vazquez et al. Bioorg. Med. Chem. Lett. 11, (2001), 187-191; Andrzejewska et al. Eur. J. Med. Chem. 37 (2002), 972-978). The most probable explanation for the considerable biological activity of halogeno derivatives of benzimidazole is their ability to interfere with cell metabolism by inhibition of enzymes that control the metabolism of protein kinases.

Protein kinases constitute a large superfamily of enzymes (more than 500 members encoded by the human genome) present in every eukaryotic and prokaryotic cell and playing a special role as regulators of cellular mechanisms. These enzymes catalyze the transfer of phosphate group from ATP or GTP to amino acids, i.e., serine, threonine or tyrosine. These are in general "quiet" enzymes, which activate themselves at individual stages of cell metabolism, including pathological stages. At present, protein kinases and particularly their inhibitors arouse the interest of researchers as potential objects that would help in the design of specific drugs. For example, Gleevec, a drug for treating chronic myeloid leukemia is a result of studies on kinase inhibitors (Druker B. J., Talpaz M., Resta D. J., Peng B., Buchdunger E., Ford J. M., Lydon Nn. B., Kantarjian H., Capdeville R., Ohno-Jones S., Sawyers C. L. N. Eng. J. Med. 344, (2001) 1031-1037).

A special family of protein kinases are the so-called casein kinases (CK1 and CK2), for which more than three hundred proteins—substrates for these enzymes—exist. They participate in many cell processes (Litchfield D. W. Biochem. J. 369, (2003) 1-15). There are many facts indicating that their subunits can act as oncogenes (Kelliher M. A., Seldin D. C., Leder P. EMBO J. 15, (1996) 5160-5166; Orlandini M., Semplici F., Feruzzi R., Meggio F., Pinna L. A., Oliviero S. J. Biol. Chem. 273, (1998) 21291-21297; Landesman-Bollag E., Channavajhala P. L., Cardiff R. D., Seldin D. C. Oncogene 16 (1998) 2965-2974). The most widely known and potent inhibitor of casein kinase 2 (CK2) is 4,5,6,7-tetrabromobenzotriazole (TBB) (Sarno et al., 2001).

SUMMARY OF THE INVENTION

The basic aspect of the invention are new derivatives of 4,5,6,7-tetrabromobenzimidazole of Formula 1:

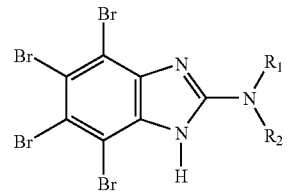

Formula 1 wherein $R_1$ is a hydrogen or an aliphatic group; and $R_2$ is an aliphatic group, optionally substituted with hydrogen or a substituent, such as, a hydroxyl group or a substituted amino group.

The following compounds are new derivatives of the present invention: 2-methylamino-4,5,6,7-tetrabromo-1H-benzimidazole, 2-dimethylamino-4,5,6,7-tetrabromo-1H-benzimidazole, 2-etanolamino-4,5,6,7-tetrabromo-1H-benzimidazole, 2-isopropyloamino-4,5,6,7-tetrabromo-1H-benzimidazole, 2-(2-hydroxypropylamino)-4,5,6,7-tetrabromo-1H-benzimidazole, and 2-(2-dimethylaminoethylamino)-4,5,6,7-tetrabromo-1H-benzimidazole.

A further aspect of the invention is a method of preparation of the new derivatives of 4,5,6,7-tetrabromobenzimidazole of Formula 1, wherein $R_1$ is a hydrogen or an aliphatic group, and $R_2$ is an aliphatic group, optionally substituted with a hydrogen or a substituent, such as, a hydroxyl group or a substituted amino group, in the reaction of a compound of Formula 2 with an amine, at elevated temperature,

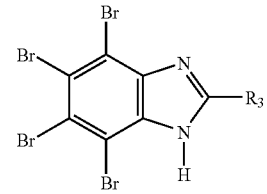

Formula 2 wherein the substituent $R_3$ is a halogen, an alkylthio group, or an alkoxy group, or any other group that is easily substituted; and the resulting product is subjected to purification by crystallization or chromatography on silica gel, and, then, treated with a mineral acid or an organic acid to convert into a salt.

In the compound of Formula 2, the substituent $R_3$ is a halogen such as Cl or Br, or an alkylthio group, such as $CH_3S$, $CH_3CH_2S$, $CH_3CH_2CH_2S$, or a lower alkoxy group, such as $CH_3O$, $C_2H_5O$, or any other group easily being substituted, such as a sulfone group or an alkylsulfoxide group.

A lower aliphatic primary amine optionally containing in the aliphatic chain additionally hydroxyl groups or substituted amino groups is used as an amine. A lower aliphatic secondary amine can also be used as an amine in the present invention. A characteristic and advantageous feature of the method of the invention is that the amine is used both as a reagent and a solvent, in aqueous or alcoholic solution and reaction of the compound of Formula 2 with amine is performed within a temperature range from 80 to 140° C.

The resulting compounds of Formula 1 can be converted by a known method into salts of mineral or organic acids.

A further aspect of the invention is a pharmaceutical composition exhibiting anti-neoplastic activity, containing an effective amount of a new compound of the invention having an anti-neoplastic activity combined with at least one inert pharmaceutically-acceptable carrier, diluent or excipient.

Compounds of the present invention can be prepared and administered in a variety of dosage forms for oral and parenteral administration. For example, compounds of the invention, can be administered through injection, i.e., as intravenous, intramuscular, intradermal, subcutaneous, intraduodenal, intraperitoneal dosage form. As regards parenteral administration, liquid unit dosage forms are prepared including each of the compounds of the invention, for example 2-dimethylamino-4,5,6,7-tetrabromo-1H-benzimidazole and aseptic vehiculum, preferably water. The above-mentioned compounds can be suspended or dissolved in vehiculum depending on a type of pharmaceutically compatible carrier. When preparing a solution, an active ingredient can be dissolved in water for injections and sterilized by filtration. The resulting sterilized solution is filled into vials or ampoules, which are then tightly closed. After filling the preparation, it can be frozen to remove water under vacuum. The resulting dry lyophilized powder is tightly closed in the vial and a second vial is attached containing water for preparation of injection solution. The compounds can be also administered by inhalation or transdermally. It is obvious for those skilled in the art that the presented dosage forms as the active ingredient can include the new compounds of the invention, as well as pharmaceutically-acceptable salts thereof.

Pharmaceutically acceptable carriers used for the preparation of pharmaceutical compositions can be liquid or solid. Solid preparation include powders, tablets, pills, capsules and dispersed granules. A solid carrier can be one or more substances, which can act as diluents, solvents, binders, preservatives, disintegrants or capsule-forming material.

A further aspect of the invention is the use of the new derivatives according to the invention for manufacturing of a drug that has an anti-neoplastic activity.

Another aspect of the invention is a method of inhibiting caseine kinase 2 activity in patients in need of such treatment by administering of an effective amount of new derivatives of the invention.

BRIEF DESCRIPTION OF THE DRAWINGS

The present invention will be more readily understood on a basis of specific examples accompanied by appended figures which are intended to illustrate the invention, and not to limit its scope, wherein.

DETAILED DESCRIPTION OF THE INVENTION

1. Pharmacological Study

The cytotoxic effect of 2-dimethylamino-4,5,6,7-tetrabromo-benzimidazole on human leukemia Jurkat T cells was studied.

Figure 1:
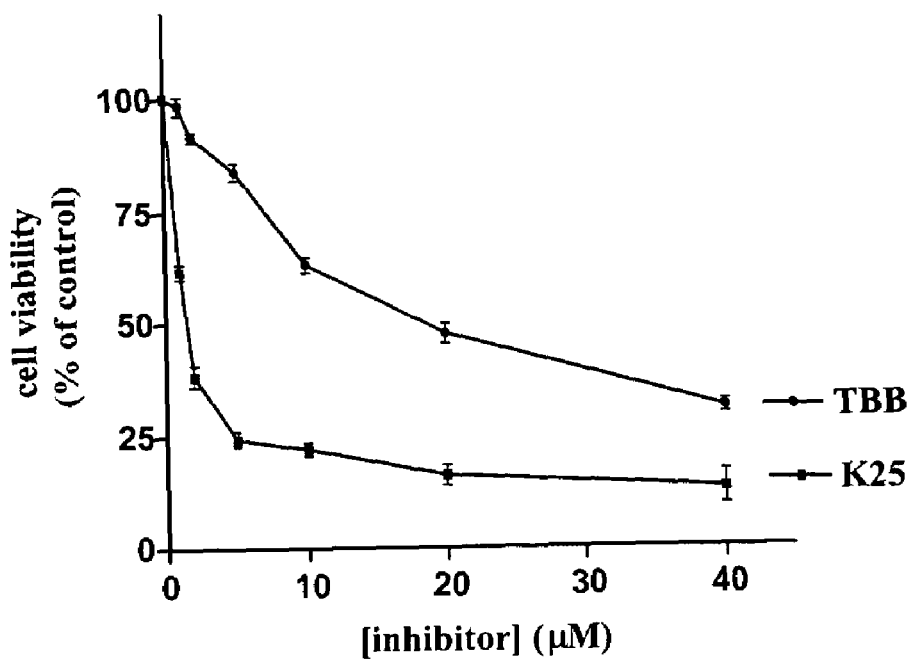
FIG. 1. illustrates cytotoxic effect of 2-dimethylamino-4,5,6,7-tetrabromobenzimidazole on human leukemia Jurkat T cells.

Leukemia Jurkat cells were incubated for 24 hours in a medium of increasing concentration of 4,5,6,7-tetrabromobenzimidazole (TBB) or 2-dimethylamino-4,5,6,7-tetrabromobenzimidazole (K25). The cytotoxic effect was assessed by means of staining with a use of MTT, (3-(4,5-dimethylthiazol-2-yl)-3,5-diphenyltriazolium bromide, reagent. Control cells were incubated in a medium with added solvent (DMSO, 05% v/v). The results were calculated as mean values of three experiments. The resulting cytotoxic effect of 4,5,6,7-tetrabromo-2-dimethylaminobenzimidazole on human leukemia Jurkat T cells is presented in FIG. 1. The results confirm that 2-dimethylamino-4,5,6,7-tetrabromobenzimidazole is several times more active than tetrabromo-benzotriazole—a well-known inhibitor of casein kinase 2.

Figure 2:
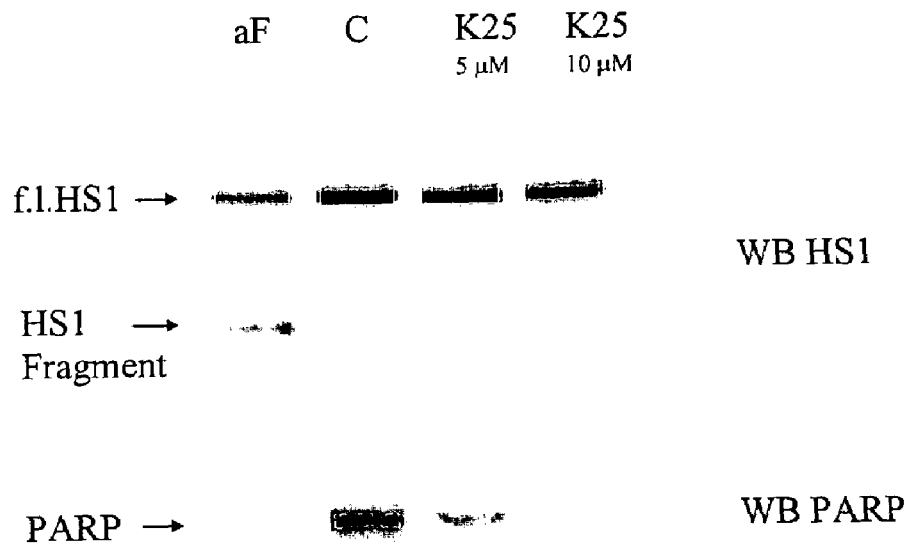
FIG. 2. illustrates mechanism of apoptosis activity of 2-dimethylamino-4,5,6,7-tetrabromobenzimidazole on human leukemia Jurkat cells by caspase activation.

Leukemia Jurkat cells were incubated for 14 hours without the addition of 2-dimethylamino-4,5,6,7-tetrabromobenzimidazole (C), and in a medium including 5 or 10 uM of 2-dimethylamino-4,5,6,7-tetrabromobenzimidazole and 50 ng/mL of antiFas (aF), a control substance to follow the apoptosis process. Activation of caspase—an enzymatic protein controlling apoptosis was found while observing degradation of two proteins—substrates of that enzyme—HS1 and PARP. The effect is presented in FIG. 2. The results indicate that molecular mechanism of action of 2-dimethylamino-4,5,6,7-tetrabromobenzimidazole can be elucidated by induction of apoptosis-programmed cell death.

Tests of enzymatic activity of kinases were carried out using methodology described by Sarno et al. 2003 and are summarized in Table 1. The residual activity was determined by incubation in the presence of inhibitor at a concentration of 10 $\mu$M and expressed as percentage activity without an inhibitor.

TABLE 1

Tests of enzymatic activity of kinases.

| No. | Kinase* | 4,5,6,7-Tetrabromo-benzotriazole (TBB) | 2-Dimethylamino-4,5,6,7-tetrabromobenzimidazole (K25) |
|---|---|---|---|
| 1. | CK1 | 91 | 87 |
| 2. | CK2 | 13 | 4 |
| 3. | G-CK | 95 | 92 |
| 4. | DYRK1a | 22 | 2 |

*CK1—casein kinase 1, CK2—casein kinase 2, G-CK—casein kinase from Golgi apparatus, DYRK1a—(Dual-specificity tyrosine phosphorylated and regulated kinase) Tyrosine kinase having regulating properties.

EXPERIMENTAL SECTION

Materials

Native CK1 (nCK1) and CK2 (nCK2) were purified from rat liver (Meggio et al., 1981); Golgi CK (G-CK), purified from rat lactating mammary gland, was provided by Dr. A. M. Brunati (Padova, Italy). Protein tyrosine kinases Lyn, c-Fgr, Syk (also termed TPK-IIB) were purified from rat spleen as previously referenced (Sarno et al., 2003). Human recombinant α and β subunits of CK2 were expressed in *E. coli* and the holoenzyme was reconstituted and purified as previously described (Sarno et al., 1996). The V66A and I174A CK2 mutants were obtained as described previously (Sarno et al., 2003). V66AI174A double mutant was obtained with the "QuikChange-SiteDirected Mutagenesis" kit (Stratagene), using human V66A cDNA α inserted in pT7-7 vector as template and two synthetic oligonucleotide primers, 5'-GCA-CAGAAAGCTACGACTAGCAGACTGGGGTTTGGC-3' and 5'-GCCAAACCCCAGTCTGCTAGTCG-TAGCTTTCTGTGC-3', each complementary to opposite strands of template. Expression and purification of the mutant was performed as previously described (Sarno et al., 2003).

*Saccharomyces cerevisiae* piD261 was provided by Dr. S. Facchin (Padova, Italy). The source of all the other protein kinases used for specificity assays is either described or referenced by Davies et al. (2000).

Kinetic Determination:

Initial velocities were determined at each of the substrate concentration tested. Km values were calculated either in the absence or in the presence of increasing concentrations of inhibitor, from Lineweaver-Burk double-reciprocal plots of the data. Inhibition constants were then calculated by linear regression analysis of Km/Vmax versus inhibitor concentration plots. Considering that all TBI derivatives behave as competitive inhibitors with respect of ATP, inhibition constants were also deduced from the $IC_{50}/K_i$ Cheng-Prusoff relationship (Cheng and Prusoff, 1973) by determining $IC_{50}$ for each compound at 1 µM ATP concentration.

CK2 Phosphorylation Assays:

Phosphorylation assays were carried out in the presence of increasing amounts of each inhibitor tested in a final volume of 25 µl containing 50 mM Tris-HCl pH 7.5, 100 mM NaCl, 12 mM $MgCl_2$, 100 µM synthetic peptide phosphorylation substrate—RRRADDSDDDDD and 0.02 µM γ-$^{33}$P-ATP (500-1000 cpm/pmole), unless otherwise indicated, and incubated for 10 minutes at 37° C. Assays were stopped by addition of 5 µl of 0.5 M orthophosphoric acid before spotting aliquots onto phosphocellulose filters. Filters were washed in 75 mM phosphoric acid (5-10 ml/each) four times then once in methanol and dried before counting.

Cell Culture, Treatment, and Viability Assay:

The human leukemia Jurkat T-cell line was maintained in RPMI-1640, supplemented with 10% (v/v) fetal calf serum, 2 mM L-glutamine, 100 units/ml penicillin and 100 ug/ml streptomycin. For the treatment, cells were suspended at a density of $10^6$ cells/ml in a medium containing 1% (v/v) fetal calf serum, then incubated at 37° C., in the presence of the compounds at the indicated concentrations. Control cells were treated with equal amounts of solvent inhibitor was solved. At the end of incubations, cells were lysed by the addition of hypoosmotic buffer, as previously described (Sarno et al., 2003).

Cell viability was assessed by means of 3-(4,5-dimethylthiazol-2-yl)-3,5-diphenyltriazolium bromide (MTT) reagent, while caspase activation was followed by Western blot monitoring of PARP and HS1 protein degradation, as previously described (Ruzzene et al., 2002).

Surprisingly, experimental data obtained as a result of the present work indicate that by retaining the benzene moiety brominated at four positions, which moiety fits well into the hydrophobic cavity in the vicinity of ATP binding site, and modifying the triazole fragment of the molecule, the newly-synthesized compounds being a subject of the invention exhibit much better properties when compared to the known 4,5,6,7-tetrabromobenzotriazole (TBB)—one of the most effective and selective inhibitors of casein kinase 2 heretofore.

It has been found that replacement of nitrogen atom at position 2 by carbon atom makes it possible to perform further modifications in that position more easily by replacement of hydrogen atom at position 2 with hydrophilic groups, which, in turn, makes it possible to establish new van der Waals interactions or form hydrogen bonding with polar kinase chains.

It appears that among the synthesized inhibitors—the benzimidazole derivatives, the most effective is 2-dimethylamino-4,5,6,7-tetrabromobenzimidazole (K25), for which inhibition constant (40 nM) is the lowest among values observed for CK2 inhibitors up to now, and is one order of magnitude lower than that for TBB. Pointed out should be the selectivity of K25, which is comparable to that of TBB, because only one kinase, i.e., DYRK1a among more than 30 kinases examined, exhibits similar susceptibility to inhibition by K25.

More important is, however, the cytotoxicity of K25, which is several times higher when compared to that of TBB in relation to leukemia Jurkat cells. K25 unlike TBB does not cause depolarization of isolated mitochondria. All of this indicates undoubtedly that K25 has greater advantages than TBB, especially for in vivo studies.

We have found experimentally that some 2-amino-4,5,6,7-tetrabromobenzimidazoles substituted by the amino group (—$NR_1R_2$), are more potent inhibitors CK2 than TBB. The respective results are summarized in Table 2. Thus, the above-mentioned 2-amino-4,5,6,7-tetrabromobenzimidazoles substituted by the amino group (—$NR_1R_2$) can be useful as potential drugs as well as test reagents in molecular biology.

TABLE 2

Efficacy of 2-amino-4,5,6,7-pentabromobenzimidazole derivatives as CK2 inhibitors.

| No. | Compound | Inhibition constant $K_i$ (µM) |
|---|---|---|
| 1. | 4,5,6,7-tetrabromobenzotriazole (TBB) | 0.30 |
| 2. | 2-amino-4,5,6,7-tetrabromobenzimidazole | 0.09 |
| 3. | 2-methylamino-4,5,6,7-tetrabromobenzimidazole | 0.09 |
| 4. | 2-dimethylamino-4,5,6,7-tetrabromobenzimidazole (K25) | 0.04 |
| 5. | 2-etanoloamino-4,5,6,7-tetrabromobenzimidazol | 0.13 |
| 6. | 2-isopropylamino-4,5,6,7-tetrabromobenzimidazole | 0.06 |
| 7. | 2-(2-hydroxy)propyloamino-4,5,6,7-tetrabromobenzimidazole | 0.14 |
| 8. | 2-dimethylaminoethylamino-4,5,6,7-tetrabromobenzimidazole | 0.16 |

Considering the state of the art that indicates high expression of casein kinase in the brain of patients suffering from Down's syndrome as well as in case of Alzheimer's disease, in which overproduction of kinases DYRK1a takes place, it seems very probable that the new drugs of the invention will be useful in the treatment of said diseases.

2. Synthesis and Characterization of Tetrabromobenzimidazole (TBI) Derivatives

All chemicals and solvents used for the synthesis were purchased from Sigma-Aldrich. Melting points (uncorr.) were measured in open capillary tubes on a Gallenkamp-5 melting point apparatus. Ultraviolet absorption spectra were recorded on Kontron Uvikon 940 spectrometer. $^1$H NMR spectra (in ppm) were measured with Varian Gemini 200 MHz and Varian UNITY plus 500 MHz spectrophotometers at 298° K in $D_6$ (DMSO) using tetramethylsilane as the internal standard. Mass spectra (70 eV) were obtained with AMD-604 (Intectra) spectrometer. Flash chromatography was performed on silica gel (Merck) (230-400 mesh). Analytical thin-layer chromatography (TLC) was carried out on pre-coated silica gel $F_{254}$ (Merck) plates (0.25 mm thickness).

EXAMPLES

Example I

2-Methylamino-4,5,6,7-tetrabromo-1H-benzimidazole

The mixture of 2-chloro-4,5,6,7-tetrabromobenzimidazole (0.94 g, 2 mmol) and methylamine (EtOH sol., 35 ml, 30%) was heated 20 h in steel autoclave at 110-115° C. The reaction mixture was evaporated to dryness and the residue crystallized from 80% EtOH to give colorless crystals (630 mg, 68%). M.p. 283-285° C. TLC ($CHCl_3$/MeOH, 9:1): Rf=0.48. $^1$H-NMR ($D_6$(DMSO)): 2.94 (d, $CH_3$), 6.69 (q, NH), 11.60 (bs, NH-benzim.). Anal. calcd. for $C_8H_5Br_4N_3$ (462.77): C, 20.76; H, 1.09; N, 9.08. Found: C, 20.70; H, 1.25; N, 8.83.

Example II

2-Dimethylamino-4,5,6,7-tetrabromo-1H-benzimidazole

The mixture of 2,4,5,6,7-pentabromobenzimidazole (1.02 g, 2 mmol) and dimethylamine (EtOH sol., 30 ml, 30%) was heated 20 h in steel autoclave at 110-115° C. The reaction mixture was evaporated to dryness and the residue crystallized from 80% EtOH to give colorless crystals (710 mg, 75%). M.p. >330° C. (decomp.). TLC ($CHCl_3$/MeOH, 9:1): Rf=0.48. $^1$H-NMR ($D_6$(DMSO)): 3.13 (s, 2×$CH_3$), 11.50 (bs, NH-benzim.). Anal. calcd. for $C_9H_7Br_4N_3$ (476.79): C, 22.67; H, 1.48; N, 8.81. Found: C, 22.71; H, 1.61; N, 8.68.

Example III

2-Ethanolamine-4,5,6,7-tetrabromo-1H-benzimidazole

The mixture of 2-methylthio-4,5,6,7-tetrabromobenzimidazole (0.96 g, 2 mmol) and ethanolamine (10 ml) was heated 8 h under reflux in the oil bath at 120° C. The reaction mixture was evaporated to dryness and the residue crystallized from 80% EtOH to give colorless crystals (610 mg, 62%). M.p. 216-218° C. TLC ($CHCl_3$/MeOH, 95:5): Rf=0.48. $^1$H-NMR ($D_6$(DMSO)): 1.05 (t, $CH_2$), 4.36 (t, $CH_2$), 4.90 (bs, OH), 6.68 (t, NH), 11.50 (bs, NH-benzim.). Anal. calcd. for $C_9H_7Br_4N_3O$ (492.79): C, 21.94; H, 1.43; N, 8.53. Found: C, 21.90; H, 1.60; N, 8.40.

Example IV

2-Isopropylamine-4,5,6,7-tetrabromo-1H-benzimidazole

The mixture of 2,4,5,6,7-pentabromobenzimidazole (1.02 g, 2 mmol) and isopropylamine (EtOH sol., 25 ml, 20%) was heated 20 h in steel autoclave at 110-115° C. The reaction mixture was evaporated to dryness and the residue crystallized from 80% EtOH to give colorless crystals (690 mg, 70%). M.p. 288-290° C. (decomp.). TLC ($CHCl_3$/MeOH, 9:1): Rf=0.74. $^1$H-NMR ($D_6$(DMSO)): 1.22 (d, 2×$CH_3$), 4.05 (m, CH), 6.60 (d, NH), 11.20 (bs, NH-benzim.). Anal. calcd. for $C_{10}H_9Br_4N_3$ (490.82): C, 24.47; H, 1.85; N, 8.56. Found: C, 24.36; H, 1.98; N, 8.40.

Example V 2-(2-hydroxypropylamino)-4,5,6,7-tetrabromo-1H-benzimidazole

The mixture of 2,4,5,6,7-pentabromobenzimidazole (1.02 g, 2 mmol) and 2-hydroxypropylamine ($H_2O$ sol., 25 ml, 10%) was heated 20 h in steel autoclave at 110-115° C. The reaction mixture was evaporated to dryness and the residue crystallized from 80% EtOH to give colorless crystals (620 mg, 61%). M.p. 258-260° C. TLC ($CHCl_3$/MeOH, 9:1): Rf=0.45. $^1$H-NMR ($D_6$(DMSO)): 1.12 (d, $CH_3$), 3.30 (m, CH), 3.83 (m, CH), 4.96 (d, OH), 6.62 (t, NH), 11.20 (bs, NH-benzim.). Anal. calcd. for $C_{10}H_9Br_4N_3O$. (506.82): C, 23.70; H, 1.79; N, 8.29. Found: C, 23.66; H, 1.88; N, 8.16.

Example VI 2-(2-Dimethylaminoethylamino)-4,5,6,7-tetrabromo-1H-benzimidazole The mixture of 2,4,5,6,7-pentabromobenzimidazole (1.02 g, 2 mmol) and dimethylaminoethylamine (EtOH sol., 25 ml, 10%) was heated 20 h in steel autoclave at 110-115° C. The reaction mixture was evaporated to dryness and the residue crystallized from 80% EtOH to give colorless crystals (580 mg, 56%). M.p. >250° C. (decomp.). TLC ($CHCl_3$/MeOH, 7:3): Rf=0.15. $^1$H-NMR ($D_6$(DMSO)): 2.29 (s, 2×$CH_3$), 2.54 (m, $CH_2$), 3.43 (q, $CH_2$), 6.82 (t, NH), 11.10 (bs, NH-benzim.). Anal. calcd. for $C_{11}H_{12}Br_4N_4$. (519.86): C, 25.41; H, 2.33; N, 10.78. Found: C, 25.56; H, 2.48; N, 10.64.

Example VII

2-Dimethylamino-4,5,6,7-tetrabromo-1H-benzimidazole hydrochloride

2-Dimethylamino-4,5,6,7-tetrabromobenzimidazole (0.48 g, 1 mmol) was dissolved by heating in EtOH (80 ml) and to this solution hydrochloric acid (36% $H_2O$ sol., 5 ml) was added. Almost immediately the microcrystalline solid begins to separate. The mixture was kept in 4° C. overnight and hydrochloride (350 mg, 68%) was separated as small needles. M.p. >330° C. (decomp.).

The invention claimed is:

1. A derivative of 4,5,6,7-tetrabromobenzimidazole of Formula 1

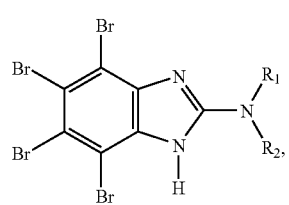

Formula 1 wherein
  $R_1$ is a hydrogen or an aliphatic group; and
  $R_2$ is an aliphatic group, optionally substituted with a substituent selected from a hydroxyl and a substituted amino group.

2. The derivative according to claim 1, which is 2-methylamino-4,5,6,7-tetrabromo-1H-benzimidazole.

3. The derivative according to claim 1, which is 2-dimethylamino-4,5,6,7-tetrabromo-1H-benzimidazole.

4. The derivative according to claim 1, which is 2-ethanolamino-4,5,6,7-tetrabromo-1H-benzimidazole.

5. The derivative according to claim 1, which is 2-isopropylamino-4,5,6,7-tetrabromo-1H-benzimidazole.

6. The derivative according to claim 1, which is 2-(2-hydroxypropylamino)-4,5,6,7-tetrabromo-1H-benzimidazole.

7. The derivative according to claim 1, which is 2-(2-dimethylaminoethylamino)-4,5,6,7-tetrabromo-1H-benzimidazole.

8. A method of preparation of a derivative of 4,5,6,7-tetrabromobenzimidazole of Formula 1

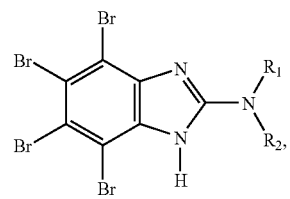

Formula 1 comprising
(a) reacting a compound of Formula 2

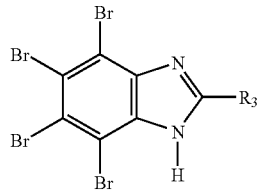

Formula 2 with an amine at an elevated temperature; and
(b) purifying the resulting product by crystallization or silica gel chromatography wherein
$R_1$ is a hydrogen or an aliphatic group;
$R_2$ is an aliphatic group, optionally substituted with a substituent selected from a hydroxyl and a substituted amino group; and
$R_3$ is a halogen, an alkylthio, an alkoxy, a sulfone or an alkylsulfoxide.

9. The method of claim 8, wherein $R_3$ is selected from the group —Cl, —Br, $CH_3S$—, $C_2H_5S$—, $C_3H_7S$—, $CH_3O$—, and $C_2H_5O$—.

10. The method according to claim 8 wherein said amine is a primary lower aliphatic amine.

11. The method according to claim 10 wherein said primary aliphatic amine includes in the aliphatic chain additionally hydroxyl groups or substituted amino groups.

12. The method according to claim 8 wherein said amine is a secondary lower aliphatic amine.

13. The method according to claim 8 wherein said amine is used both as a reagent and as a co-solvent in an aqueous or alcoholic solution.

14. The method according to claim 8 wherein the reaction of said compound of Formula 2 with said amine is carried out at a temperature in the range between 80 to 140° C.

15. A pharmaceutical composition exhibiting an anti-leukemic activity comprising a pharmaceutically-effective amount of a derivative of 4,5,6,7-tetrabromobenzimidazole of Formula 1

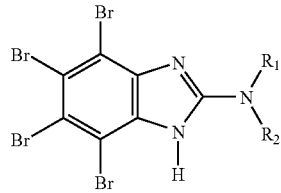

Formula 1 and at least one inert, pharmaceutically acceptable carrier or diluent wherein
$R_1$ is a hydrogen or an aliphatic group; and
$R_2$ is an aliphatic group, optionally substituted with a substituent selected from a hydroxyl and a substituted amino group.

16. The pharmaceutical composition of claim 15, wherein said derivative of 4,5,6,7-tetrabromobenzimidazole of Formula 1 is selected from the group consisting of 2-methylamino-4,5,6,7-tetrabromo-1H-benzimidazole; 2-dimethylamino-4,5,6,7-tetrabromo-1H-benzimidazole; 2-ethanolamino-4,5,6,7-tetrabromo-1H-benzimidazole; 2-isopropylamino-4,5,6,7-tetrabromo-1H-benzimidazole; and 2-isopropylamino-4,5,6,7-tetrabromo-1H-benzimidazole; 2-(2-hydroxypropylamino)-4,5,6,7-tetrabromo-1H-benzimidazole; and 2-(2-dimethylaminoethylamino)-4,5,6,7-tetrabromo-1H-benzimidazole.

17. A method of inhibiting caseine kinase 2 activity in a patient in the need of such treatment whereby human leukemia is treated, comprising administering to said patient a pharmaceutically-effective amount of the compound of Formula 1

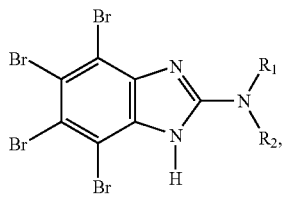

Formula 1 wherein
$R_1$ is a hydrogen or an aliphatic group; and
$R_2$ is an aliphatic group, optionally substituted with a substituent selected from a hydroxyl and a substituted amino group.

18. The method of claim 17, wherein said compound of Formula 1 is selected from the group consisting of 2-methylamino-4,5,6,7-tetrabromo-1H-benzimidazole; 2-dimethylamino-4,5,6,7-tetrabromo-1H-benzimidazole; 2-ethanolamino-4,5,6,7-tetrabromo-1H-benzimidazole; 2-isopropylamino-4,5,6,7-tetrabromo-1H-benzimidazole; and 2-isopropylamino-4,5,6,7-tetrabromo-1H-benzimidazole; 2-(2-hydroxypropylamino)-4,5,6,7-tetrabromo-1H-benzimidazole; and 2-(2-dimethylaminoethylamino)-4,5,6,7-tetrabromo-1H-benzimidazole.

19. A method of treating human leukemia in a patient in the need of such treatment comprising administering to said patient a pharmaceutically-effective amount of the compound of Formula 1

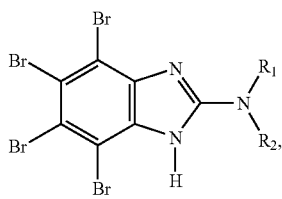

Formula 1 wherein
R₁ is a hydrogen or an aliphatic group; and
R₂ is an aliphatic group, optionally substituted with a substituent selected from a hydroxyl and a substituted amino group.

20. The method of claim 19, wherein said compound of Formula 1 is selected from the group consisting of 2-methylamino-4,5,6,7-tetrabromo-1H-benzimidazole; 2-dimethylamino-4,5,6,7-tetrabromo-1H-benzimidazole; 2-ethanolamino-4,5,6,7-tetrabromo-1H-benzimidazole; 2-isopropylamino-4,5,6,7-tetrabromo-1H-benzimidazole; and 2-isopropylamino-4,5,6,7-tetrabromo-1H-benzimidazole; 2-(2-hydroxypropylamino)-4,5,6,7-tetrabromo-1H-benzimidazole; and 2-(2-dimethylaminoethylamino)-4,5,6,7-tetrabromo-1H-benzimidazole.

* * * * *